United States Patent

Hornack

[11] Patent Number: 6,063,406
[45] Date of Patent: May 16, 2000

[54] SKIN CARE COMPOSITIONS

[75] Inventor: Richard S. Hornack, Overland Park, Kans.

[73] Assignee: Chemcraft, Inc., Overland Park, Kans.

[21] Appl. No.: 09/062,094

[22] Filed: Apr. 17, 1998

Related U.S. Application Data

[60] Provisional application No. 60/044,648, Apr. 18, 1997.

[51] Int. Cl.$^7$ .......................... A61K 33/00; A61K 33/14; A61K 33/42; A61K 35/78; A61K 47/30
[52] U.S. Cl. .......................... 424/678; 424/600; 424/601; 424/603; 424/606; 424/717; 424/195.1; 514/772; 514/772.3; 514/847; 514/861; 514/862; 514/863; 514/864; 514/865; 514/886; 514/887; 514/944; 514/947
[58] Field of Search ................................. 424/678, 195.1, 424/600, 601, 603, 606, 717, 613; 514/847, 861–865, 886–887, 944, 947, 772, 772.3

[56] References Cited

U.S. PATENT DOCUMENTS

| | | |
|---|---|---|
| 5,306,511 | 4/1994 | Whang . |
| 5,466,680 | 11/1995 | Rudy ............................................ 514/57 |
| 5,849,346 | 12/1998 | Hornack ...................................... 426/66 |

OTHER PUBLICATIONS

Whang, Reverse Aging, 1990, pp. 74, 75 and 78, JSP Publishing, Miami, Florida.
Exchange, Fundamentals of Deionization by Ion Exchange, date printed Aug. 13, 1998, WorldWideWeb, http://www.culliganmiami. com/pf5.html.
The Basics of Ionic Water, date printed Aug. 13, 1998, pp. 1–13, WorldWideWeb, http://www.goodwaterco.com/ionized.html.

*Primary Examiner*—John Pak
*Attorney, Agent, or Firm*—Crowe & Dunlevy, P.C.; Bill D. McCarthy; Phillip L. Free, Jr.

[57] ABSTRACT

The present invention includes a process and composition for treating skin disorders. The composition of the present invention comprises 94.0 to 99.2 percent by weight of cation-free water, 0.1 to 1.0 percent by weight of Calcium chloride, 0.0 to 2.0 percent by weight of linear long chain polyphosphate, 0.1 to 1.0 percent by weight of sodium bicarbonate and 0.5 to 3.0 percent by weight of cross-linked polyacrylamide polymer.

8 Claims, No Drawings

SKIN CARE COMPOSITIONS

RELATED APPLICATIONS

This application claims priority to U.S. Provisional Application Ser. No. 60/044,648 filed Apr. 18, 1997, hereby incorporated by reference.

BACKGROUND OF THE INVENTION

1. Field of the Invention

The present invention relates to compositions and methods for treatment of dermal ailments, such as blemishes, pimples, cuts, scrapes, burns, scars, scalp conditions and chicken pox, using pH properties of the present composition.

2. Description of the Prior Art

Skin conditions that result in pimples, acne, blackheads, blemishes and redness of the skin are caused by clogged conditions of the skin known as comedones. When this condition occurs, inflamation results causing, papules, pustules and cysts. Comedo disruption generally results in subsequent ruptures.

For years treatment of these conditions has been primarily topical and through the use of substances such as benzol peroxide, vasoconstrictors, salicylic acid, retinoic acid, azelaic acid, lactic acid, glycolic acid, pyreuric acid, tannins, benzlidenecamphor and derivatives thereof, alpha hydroxyis, surfactants, and other irritating substances. In most cases, the prior art approaches have coupled these substances with other materials which are present to ameliorate the radical irritating effects of the primary therapeutic agent. Patents have been issued for improvements on these agents and carriers, providing better coverage, penetration or less irritating effects.

Most of these formulas, however, also contain ingredients which do not lend themselves to the natural rapid healing abilities of the body. For examnple, ingredients such as alcohol (which causes dryness and prevents cells from initiating the rehabilitation process); acids (which allow the alcohol to dry at deeper levels of penetration); propylene glycol (which further clogs the skin pores); fragrances (which can be irritating and cause allergic reaction) organic and metal salts (which cannot be readily absorbed and will adhere to the skin and clog pores) are used in preparations to heal and treat skin.

Conditions such as cuts, scrapes, skin abrasions and burns are typically treated with pharmaceutical products containing antibiotics. Such products are generally used to provide an antibacterial medium to prevent infection. For skin maladies such as dry skin, ichthyosis, eczema, palmar keratoses, plantar kerotoses, dandruff, acne, warts, herpes, pruritts, psoriasis, age spots, wrinkles; and disturbed keratinization, alpha hydroxy is often used. Alpha hydroxy however, is a known irritant. Solvent materials such as ethanol, polyethylene, glycol, polypropylene, glycol, propylene glycol, glycerol, 1, 2, 4 butanetriol, ethanol, isopropanol, and butanediol may also be used. Furthermore, a variety of surfactants such as isoceteth-20, sodium methyl cocoyl and aurate, sodium methyl oleoyl taurant, sodium laurel sulfate are prevalent in prior art.

The irritation is compounded in the prior art by the addition of irritating components such as hydroquinone, kojic acid, antioxidants; chelators and sequestrants; thickening agents; acrylic acids; colorings, fragrances; pigments; astringents; witch hazel distillate; and urea.

Thus, in the past, cuts and other dermal disorders were treated topically with ointments and cremes designed to facilitate the healing process of the skin. Typically these ointments and cremes worked on cuts and scrapes by forming a scab on the afflicted area while causing irritation. There is a need, however, for a composition to treat such dermal disorders which will facilitate healing from the inside out with little to no irritation.

SUMMARY OF INVENTION

The present invention provides a composition and method for the treatment of dermal disorders healing through penetration of the epidermis during topical application thereby allowing internal healing.

It is a general object of the present invention to provide compositions that treat dermal disorders by penetrating the epidermis and providing damaged nuclei with moisture, healing electrolytes, and other healing elements.

A further object of the present invention is to provide a composition and methods which treat dermal disorders without irritation or other allergic reactions.

Another object of the present invention is to provide a composition and method that creates an optimal pH range for penetration and rapid healing from inside of the cell while preventing infection of a damaged skin area.

Other objects, features, and advantages of the present invention will become clear from the following description when read in conjunction with the appended claims.

DETAILED DESCRIPTION OF THE PREFERRED EMBODIMENT

The DNA and RNA of the human body remember the history of a cell when reproducing. Therefore, with irritations such as blemishes and even skin cancers, new irritation or disorders may reappear in spots on the body where they have appeared before. The present invention, through penetration of the cell wall and nuclei, replaces valuable components and allows the RNA and DNA to return to the original memory of skin which has not been damaged.

It is important then to remove dead cells and to repair damaged cells by replacing as much moisture at cellular levels as possible as impacts on the skin surfaces by pollutants, irritants, accidents, and ultra violet rays damage the skin during the aging process. Incorporating moisture into the cell and penetrating the cell through the treated water of the present invention can deliver healing moisture and other materials to the cell through carriers such as ozonation and electrolytes.

The present invention provides a composition and method for the treatment of dermal disorders which can be applied topically and without irritation.

Referring now to the present invention, one embodiment of the composition of the present invention is summarized in Table 1 below.

TABLE 1

| Component | Percent by Weight |
| --- | --- |
| Treated Water (50 to 98% free of cationic minerals) (with optional ozonation) | 94.0 to 99.2 |
| Linear long chain polyphosphate | 0.0 to 2.0 |
| Calcium chloride | 0.1 to 1.0 |
| Sodium bicarbonate | 0.1 to 1.0 |
| Cross-linked polyacrylamide polymer | 0.5 to 3.0 |

The composition of the present invention is produced by first removing fifty percent to ninety-eight percent of all mineral cations from tap water either by electrochemical reaction or by ultra filtration through a strong anionic resin bed. After removal of the cations without removing any of the anionic charged material, the treated water with a pH range of 3.0 to 4.5, may be further treated through the process of ozonation. The treated water then serves as a base for mixing zero percent to two percent by weight of linear long chain polyphosphate, one-tenth percent to one percent by weight of calcium chloride, one-tenth percent to one percent by weight of sodium bicarbonate and five-tenths percent to three percent by weight of cross linked polyacrylamide polymer into the solution. The composition may be in liquid, gel, spray, ointment, or cream form.

The addition of the cross-linked polymers create a gel that facilitates penetration of the invention through the epidermis of the skin. Other embodiments may include a variety of non-carcinogenic, non-irritating healing materials that facilitate the carrier properties of the present invention. Such healing materials include nutrients, minerals, vitamins, electrolytes, amino acids, enzlimes, herbs, plant extracts, glandular or animal extracts, or safe synthetic therapeutic agents that may be added to the treated water base to facilitate the healing of dermal disorders. Any synthetic or naturally occurring suitable base and carrier material may be used to produce pastes, poultices, mousses, sprays, sticks, gels, powders, cosmetics, creams, and liquid-gels for use as ointments, skin and hair conditioners, scalp treatments, skin cleaners or soaps.

Topically applying the present embodiment of Table 1 may be used for skin maladies such as sunburns by applying the formula over the entire burned area and allowing the formula to soak into the skin and penetrate the cell walls. Thereafter, applying the liquid aloes and allowing the aloe to dry will add moisture within the cell, while exfoliating the damaged dead top layers. The process mall be repeated as desired for up to twenty-four hours for an increased healing effect and reduction of heat inside the cells and the body. After twenty-four hours, moisturizing, non-irritating oils or creams may be applied.

For severe burns, the preferred medium of the present invention is a liquid or liquid-gel base, for soaking the affected area. The soaking period can last for five minutes and can be repeated as often as every thrity minutes, depending upon the severity of the situation. For minor burns, topical application of the formula as shown in Table 1 or 2 on a repeated basis will heal the area rapidly.

In an alternative embodiment, the present invention is directed toward the use of calendula extract to treat cuts, scrapes, burns, scars and chicken pox. The composition is summarized in Table 2.

TABLE 2

| Component | Percent by Weight |
| --- | --- |
| Treated Water (50 to 98% free of cationic minerals) (with optional ozonation) | 93.2 to 99.19 |
| Linear long chain polyphosphate | 0.0 to 2.0 |
| Calcium chloride | 0.1 to 1.0 |
| Sodium bicarbonate | 0.1 to 1.0 |
| Cross-linked polyacrylamide polymer | 0.5 to 3.0 |
| Calendula extract | 0.01 to 1.0 |

In this embodiment, the water which has been treated to remove fifty to ninety-eight percent of the mineral cations serves as a base for mixing zero to two percent by weight linear long chain polyphosphate, one-tenth to one percent by weight calcium chloride, and one-tenth to one percent by weight sodium bicarbonate. One-hundredth percent to one percent of calendula extract is added prior to mixing the cross-linked polyacrylamide polymer to the solution. The present embodiment provides healing effects particularly useful in the treatment of cuts, scrapes, burns, scars and chicken pox.

The present invention differs from prior art approaches in several significant aspects. While the prior art approaches concentrate primarily on the healing of the dermal disorders externally by forming a scab, this invention heals internally by penetrating the epidermis and affecting cells adjacent to the problem areas. The selected electrolytes in the composition provide the penetrating properties of the composition.

The present invention also avoids the use of potentially irritating ingredients and vasoconstrictors in reducing redness on irritations and blemishes, thereby allowing the natural healing for eradicating skin irritations such as pimples.

The embodiments of the present invention as disclosed in Tables 1 and 2 may be utilized for deep cuts. The method of application begins with applying the present invention topically before using a bandage to stop the bleeding. The present invention will begin to work under the bandaged area until the wound has been completely healed. The cuts will often heal without scabbing or scarring if the composition of the present invention is applied immediately after the damage has occurred and if repeated applications are made.

The invention as disclosed in Table 1 or 2 may also be used to heal new as well as old scars. The number of applications on the area will depend upon the severity of the scar and the time available for treatment. Scars can disappear rapidly with multiple applications daily, or over time with only one or two applications daily. The present invention has healed scars as old as eight years through topical application of the formula as shown in Table 1 to the scarred area and surrounding tissue ten to twelve times daily. Total healing of these scars took less than four months. One subject, with a two and a half inch scar across his neck, experienced pain as well as lack of hair growth at the scarred area for over ten years. The subject applied the formula as shown in Table 1, up to twice a day. Within two weeks, the pain was substantially reduced while the hair grew into the area within one month. Yet another subject in his teens was able to heal an eight year old scar under the chin with intermittent applications of the formula shown in Table 1. Even without daily applications, the scar disappeared within two months.

The invention as disclosed may also be used to treat chicken pox. Applying the present invention as disclosed in Tables 1 and 2 at the onset and over the first three to five days over the entire skin area, or at every point that a discoloration or irritation begins will allow instant cellular repair. Therefore, instant application will prevent itching and the formation of the chicken pox bumps. If the chicken pox already have progressed such that discolored bumps have formed, applying the invention disclosed herein repeatedly will stop the itching. Subjects who have applied the present invention throughout the duration of the chicken pox have suffered less skin discomfort and have experienced no scarring.

The present invention as disclosed in Table 1 may also aid in the reduction of fine line wrinkles. Applying the formulation as shown in Table 1 or a variation thereof to the area affected at least twice a day will cause fluids and electrolytes to penetrate the cell. The penetration thereafter causes swelling and regeneration of the dehydrated tissues. Applying an appropriate moisturizer or oil allows the moisturizers and other healing oils to follow the path of the formula and be delivered to the appropriate cell and nuclei and surface sites.

The formulation as shown and variations thereof is not limited to the skin disorders discussed herein and may be applied to a variety of other skin disorders. Treatment is further illustrated by the following example.

EXAMPLE

A solution is mixed according to the above description according to the specifications listed in Table 3.

TABLE 3

| Component | Amount |
| --- | --- |
| Treated Water (50 to 98%, free of cationic minerals) | 1 Liter |
| Linear long chain polyphosphate | 2.0 mg |
| Calcium chloride | 1.0 mg |
| Sodium bicarbonate | 1.0 mg |
| Cross-linked polyacrylamide polymer | 9.0 g |

The composition according to the present invention is used by applying a small portion of the composition onto the afflicted area. The composition will penetrate the skin, allowing its healing properties to work from the inside out. When used in this manner three to four times per day, for example to treat blemishes, the blemish as well as the entire afflicted area is dramatically reduced in size within the first twenty-four hours after treatment. The present invention then allows the normal skin color to resume such that the normal appearance is restored.

It is clear that the present invention is well adapted to carry out the objects and to obtain the ends and advantages mentioned as well as those inherent therein. While a presently preferred embodiment of the invention has been described for purposes of this disclosure, it will be recognized that numerous changes may be made which will readily suggest themselves to those skilled in the art and which are encompassed within the spirit of the invention disclosed and as defined in the appended claims.

What is claimed is:

1. A composition for treating skin comprising:
    94.0 to 99.2 percent by weight of tap water treated by removing 50 to 98 percent of the mineral cations;
    0.1 to 1.0 percent by weight of Calcium chloride;
    0.0 to 2.0 percent by weight of linear long chain polyphosphate;
    0.1 to 1.0 percent by weight of sodium bicarbonate; and
    0.5 to 3.0 percent by weight of cross-linked polyacrylamide polymer.

2. A composition of claim 1 wherein the pH is in the range of about 3.0 to 4.5.

3. A composition for treating skin comprising:
    93.2 to 99.19 percent by weight of tap water treated by removing 50 to 98 percent of the mineral cations;
    0.1 to 1.0 percent by weight of Calcium chloride;
    0.0 to 2.0 percent by weight of linear long chain polyphosphate;
    0.1 to 1.0 percent by weight of sodium bicarbonate;
    0.5 to 3.0 percent by weight of cross-linked polyacrylamide polymer; and
    0.01 to 1.0 percent by weight of calendula extract.

4. The composition of claim 3 wherein the pH is in the range of about 3.0 to 4.5.

5. A method of providing a topical healing solution comprising the steps of:
    removing fifty to ninety-eight percent of the mineral cations from a tap water sample by electrochemical reaction;
    treating the water through ozonation;
    providing 94.0 to 99.2 percent by weight of the water;
    adding 0.1 to 1.0 percent by weight of Calcium chloride to the water;
    adding 0.0 to 2.0 percent by weight of linear long chain polyphosphate to the water;
    adding 0.1 to 1.0 percent by weight of sodium bicarbonate to the water; and
    mixing 0.5 to 3.0 percent by weight of cross-linked polyacrylamide polymer in the water.

6. The method of claim 5 wherein the solution has a pH in the range of about 3.0 to 4.5

7. A method of providing a topical healing solution comprising the steps of:
    removing fifty to ninety-eight percent of the mineral cations from tap water;
    treating the water through ozonation;
    providing 93.2 to 99.19 percent by weight of the water;
    adding 0.1 to 1.0 percent by weight of Calcium chloride to the water;
    adding 0.0 to 2.0 percent by weight of linear long chain polyphosphate to the water;
    adding 0.1 to 1.0 percent by weight of sodium bicarbonate to the water;
    adding 0.5 to 3.0 percent by weight of cross-linked polyacrylamide polymer to the water; and
    mixing 0.01 to 1.0 percent by weight of calendula extract in the water.

8. The method of claim 7 wherein the solution has a pH in the range of about 3.0 to 4.5.

* * * * *